United States Patent [19]

Atkinson et al.

[11] Patent Number: 4,759,786
[45] Date of Patent: Jul. 26, 1988

[54] SEPARATION OF GASEOUS MIXTURES

[75] Inventors: Timothy D. Atkinson; John T. Lavin, both of London; David T. Linnett, Hoddesdon, all of England

[73] Assignee: The BOC Group plc, Windlesham, England

[21] Appl. No.: 945,439

[22] Filed: Dec. 22, 1986

[30] Foreign Application Priority Data

Dec. 23, 1985 [GB] United Kingdom ............... 8531686

[51] Int. Cl.$^4$ .............................................. F25J 3/02
[52] U.S. Cl. .................................. 62/24; 62/32; 62/36; 62/42
[58] Field of Search .................. 62/23, 24, 32, 36, 42

[56] References Cited

U.S. PATENT DOCUMENTS

| 2,768,118 | 10/1956 | Laurence et al. | 62/23 |
| 2,888,807 | 6/1959 | Bocquet | 62/23 |
| 3,313,724 | 4/1967 | Kniel | 62/24 |
| 3,518,165 | 6/1970 | Ward | 203/78 |
| 4,318,723 | 3/1982 | Holmes et al. | 62/20 |

FOREIGN PATENT DOCUMENTS

| 479106 | 4/1936 | United Kingdom . |
| 523139 | 5/1940 | United Kingdom . |
| 707173 | 4/1954 | United Kingdom . |
| 958828 | 5/1964 | United Kingdom . |
| 998822 | 7/1965 | United Kingdom . |
| 1478459 | 6/1977 | United Kingdom . |
| 2107597 | 5/1983 | United Kingdom . |
| 2174916 | 5/1986 | United Kingdom . |

OTHER PUBLICATIONS

Natural Gas Processing and Utilization Conference—"Cryogenic Removal of Carbon Dioxide from Natural Gas"—G. C. Schianni pp. 1-50-1-55.

Primary Examiner—Ronald C. Capossela
Attorney, Agent, or Firm—R. Hain Swope; Larry R. Cassett

[57] ABSTRACT

An incoming stream of gas mixture typically comprising methane and up to 12% by volume of carbon dioxide is subjected to rectification in a first column to form a carbon dioxide depleted fraction that is withdrawn as product from the top of the column and a carbon dioxide-enriched fraction which is withdrawn from the bottom of the column is warmed in a heat exchanger and is introduced into a second rectification column operating at a higher pressure than the first column. A stream in which carbon dioxide predominates is withdrawn from the bottom of the higher pressure column while a stream 34 containing a lower proportion of carbon dioxide than said enriched fraction is withdrawn from the top of the higher pressure column is throttled through a valve and is united with the incoming stream of gas mixture upstream of or in the lower pressure column.

11 Claims, 5 Drawing Sheets

SEPARATION OF GASEOUS MIXTURES

BACKGROUND TO THE INVENTION

This invention relates to the separation of gaseous mixtures. It is particularly concerned with the separation of gaseous mixtures comprising carbon dioxide and methane to form a product gas having a reduced concentration of carbon dioxide.

It is well known to purify gas mixtures comprising at least one hydrocarbon and carbon dioxide by absorbing the carbon dioxide in a suitable liquid. The capital and running costs of such purification plant tend to increase rapidly with increasing concentration of carbon dioxide. Moreover, liquids employed as absorbents tend to be corrosive, and thus relatively high maintenance costs are typically associated with such plants. Accordingly, other methods of separating hydrocarbons from carbon dioxide have been proposed. Among such other methods are those involving liquefaction of the gas mixture and fractional distillation of the liquid to produce a product vapour fraction relatively lean in carbon dioxide.

Where a mixture of methane and carbon dioxide contains relatively small proportions of carbon dioxide, say, less than 1% by volume the carbon dioxide is typically removed by adsorption, for example using a molecular sieve. It has been alternatively proposed to subject the mixture to distillation at a pressure of about 650 psia after preliminary treatment to remove any such impurities as hydrogen sulphide and mercaptans that are present in the incoming gas mixture and to reduce the temperature of the mixture to a point at which it is fully saturated or at least partially liquefied. By performing such a distillation the bulk of the gas may be removed from the top of the distillation column free from carbon dioxide while a liquid fraction including 12% by volume of carbon dioxide is removed from the bottom of the column. The phase diagram of the carbon dioxide-methane system at 650 psia is such that at carbon dioxide concentrations above 12% by volume, solid carbon dioxide will be deposited. Thus, no more than 12% by volume of carbon dioxide is included in the liquid fraction, and hence if the process is used to treat a mixture containing more than about 1% by volume of carbon dioxide there will be a substantial loss of product gas which will increase with increasing carbon dioxide concentration in the incoming gas mixture. The process, therefore, is not suitable for treatment of carbon dioxide-methane mixtures containing more than about 1% by volume of carbon dioxide.

Fractional distillation has also been employed to separate a carbon dioxide product from natural gas relatively rich in carbon dioxide (e.g. containing more than 20% by volume of carbon dioxide). In this instance, in order to avoid deposition of solid carbon dioxide, the distillation is performed at a higher pressure, typically 750 psia. However, at such pressures, owing to the nature of the phase relationships within the methane-carbon dioxide system, it is impossible to produce pure methane, and typically the liquid fraction contains substantially pure carbon dioxide and the vapour fraction about 12% carbon dioxide. This process is thus unsuitable if it is desired to obtain a methane product relatively free of carbon dioxide.

It has been proposed to provide greater operational flexibility in such fractional distillation processes by adding to the gaseous mixture of carbon dioxide and methane a substance that inhibits the deposition of solid carbon dioxide. (See, for example, U.S. Pat. specification No. 4,318,723). By this means it is possible to take a feedstock that contains a relatively high proportion of carbon dioxide and obtain a product methane fraction containing less than 12% by volume of carbon dioxide. However, such measures are not entirely satisfactory as they involve substantial capital and operating cost to separate and recycle the inhibitor. There is also added expense in providing and storing the inhibitor.

An improved process for removing high concentrations of carbon dioxide from a gas mixture comprising carbon dioxide and methane was proposed by G. C. Schianni at the Natural Gas Processing and Utilisation Conference of 1976. In this process a raw gas containing 75% mole per cent of carbon dioxide is cooled and is then passed to a high pressure column, operating at about 52 bar (i.e. above the critical pressure of methane). The bottom product consists of liquid carbon dioxide almost free of methane. The fraction collecting at the top of the high pressure column contains more than 90 mole per cent of methane. It is expanded isenthalpically and then fed to a lower pressure column operating at a pressure near to but below 46.4 bar. The liquid fraction collecting at the bottom of the low pressure column contains about 12% by volume of carbon dioxide. It is pumped to the high pressure column and thus loss of product methane in this fraction is avoided. The vapour fraction collecting at the top of the lower pressure column contains only traces of carbon dioxide and is thus taken as product. It will therefore be appreciated that unlike other fractional distillation processes for separating mixtures of carbon dioxide and methane the process described by Schianni enables a relatively high purity methane product to be produced in high yield. Previous processes had either sacrificed yield for purity or purity for yield. The process proposed by Schianni is only suitable for the treatment of mixtures of carbon dioxide and methane having a relatively large carbon dioxide concentration. Schianni states that below about 30 mole per cent of carbon dioxide, the utilitites consumptions of conventional removal systems (of the adsorption kind) are less than that of his distillation process.

It can thus be seen that all the distillation processes proposed to date are for very low carbon dioxide concentrations, e.g. less than 1%, or for higher carbon dioxide concentrations, e.g. greater than 20%, or necessitate the use of an additive.

There is thus a need for an improved process and apparatus for the separation of a methane-carbon dioxide mixture containing up to about 12% by volume of carbon dioxide, and this invention aims at meeting this need.

THE INVENTION

According to the present invention there is provided a method for separating a gaseous mixture comprising carbon dioxide and methane, including the steps of feeding said mixture into a first liquid-vapour contact column, performing a first rectification of the mixture at a lower pressure in the first liquid-vapour contact column to form a product vapour fraction containing a reduced concentration of carbon dioxide at the top of the column and a fraction enriched in carbon dioxide at the bottom of the column, subjecting the said carbon dioxide-enriched fraction to a second rectification in a second liquid-vapour contact column operating at a higher pressure than said first column and thereby forming at the bottom of the second column a liquid fraction in which carbon dioxide predominates, and at the top of the second column a vapour fraction containing a lower proportion of carbon dioxide than the said carbon dioxide-enriched fraction, and returning fluid from at or near the top of the second column to the first column, the concentrations of the carbon dioxide in the said gaseous mixture and in the said carbon dioxide-enriched fraction and the operating pressures in the columns being selected so as to avoid the deposition of solid carbon dioxide.

The invention also provides apparatus for performing the said method, said apparatus including a first rectification column having an inlet for the feed mixture, a first outlet at or near its top for a product fraction containing a reduced concentration of carbon dioxide, a second outlet at or near its bottom for a fraction enriched in carbon dioxide, pumping means for transferring a stream of said carbon dioxide-enriched fraction to the inlet of a second rectification column adapted to operate at a higher pressure than said first column, said second column having a first outlet at or near its bottom for a fraction in which carbon dioxide predominates, and a second outlet which is at or near its top for a fraction containing less carbon dioxide than the said carbon dioxide-enriched fraction, and which communicates with said first column.

Whereas plural column cryogenic processes normally have successive columns operating at progressively reducing pressure, the method and apparatus according to the invention are operated in the reverse manner with the gaseous mixture for separation being rectified in the lower pressure column, and then the resulting carbon dioxide enriched fraction being further rectified in the higher pressure column.

As will be described below with reference to the accompanying drawings, there are upper limits on the concentrations of carbon dioxide that can be tolerated in the gaseous mixture for separation and the carbon dioxide enriched fraction. The limits will tend to vary according to whether or not the gaseous mixture contains additional gases such as nitrogen and higher hydrocarbons. Where no such additional gas is present, the carbon dioxide enriched fraction at a typical operating pressure in the lower pressure column of about 41.4. atmospheres absolute may contain up to 12% by volume of carbon dioxide without it depositing solid carbon dioxide in the lower pressure column. The gaseous mixture for separation will therefore contain a smaller proportion of carbon dioxide, and typically the method and apparatus according to the invention may be used to separate a gaseous mixture of methane and carbon dioxide containing from 1 to 12% by volume of carbon dioxide and preferably one containing no more than 10% by volume of carbon dioxide. The presence of such constituents as nitrogen and hydrocarbons will tend to have some effect on the maximum amount of carbon dioxide that can be tolerated in the carbon dioxide-enriched fraction and hence will have a corresponding effect on the maximum concentration of carbon dioxide in the feed gas mixture that can be economically catered for.

Any gaseous impurity such as water hydrogen sulphide or mercaptan may be removed from the gaseous mixture upstream of its introduction into the lower pressure rectification column.

The method and apparatus according to the invention is particularly suitable for use to treat a natural gas stream that has also to be subjected to a cryogenic or low temperature nitrogen rejection process. In such a process, nitrogen present in the "raw" natural gas is separated from the natural gas in one or more rectification columns. The method according to the invention can be economically integrated with such a nitrogen rejection process in a single plant.

The method and apparatus according to the invention make it possible to reduce substantially the concentration of carbon dioxide in a mixture of methane and carbon dioxide including up to about 12% by volume carbon dioxide without any substantial loss of methane.

BRIEF DESCRIPTION OF THE DRAWINGS

The method and apparatus according to the present invention will now be described by way of example with reference to the accompanying drawings, in which.

DESCRIPTION OF PREFERRED EMBODIMENTS

Figure 1:
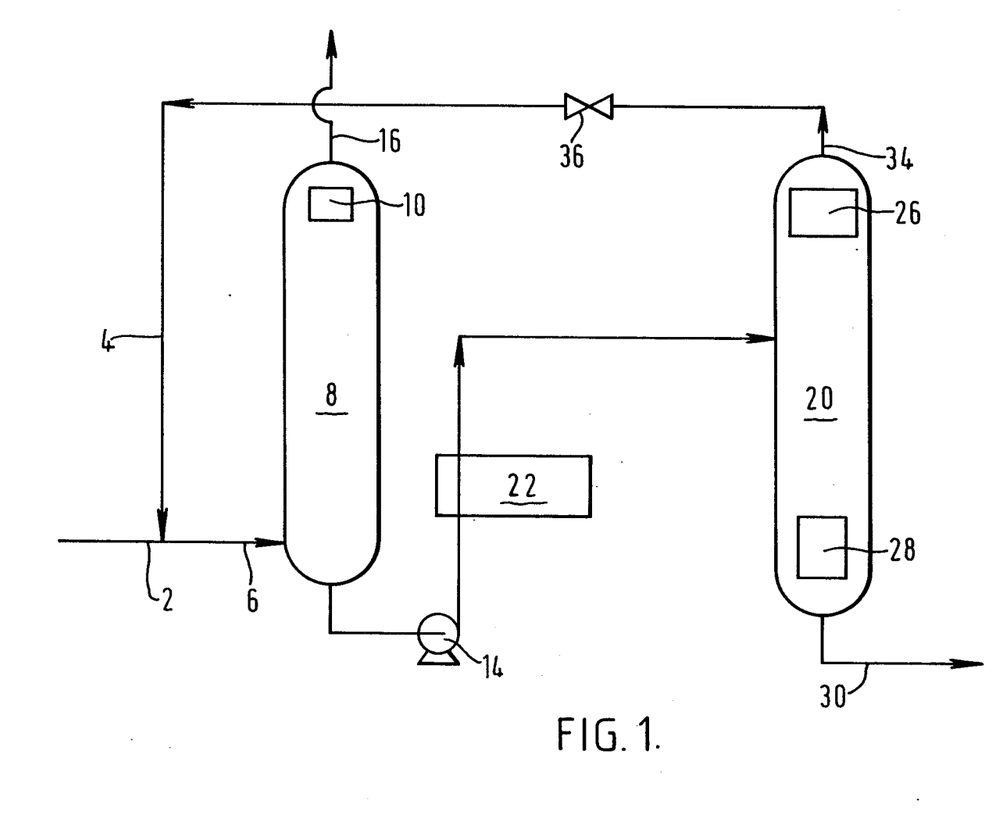
FIG. 1 is a schematic flow diagram illustrating one plant for performing the invention.

A feed stream of a mixture of carbon dioxide and methane is cooled from ambient temperature (by means not shown) to a temperature at or near its dew point and is passed to a pipeline 2 communicating with the inlet 6 of a first rectification column 8. The stream is united with a second stream comprising carbon dioxide and methane at the union of the pipeline 2 with a pipeline 4 through which the said second stream flows. Both streams are at a pressure of, say, 41.4 atmospheres. Their respective temperatures and compositions are typically such that after mixing the resulting mixture lies on/or just to the left of the line AB in FIG. 2 and does not have a temperature above that of the point B. The resultant mixture then passes through the inlet 6 into first recification column 8 fitted with a condenser 10. The rectification column 8 in this example is operated at an average pressure of 41.4 atmospheres absolute. In the rectification column 8, ascending vapour comes into intimate mass exchange relationship with a descending liquid. The column 8 may be provided with trays or with a packing (not shown) in order to facilitate this contact between the liquid and the vapour. The liquid becomes Progressively richer in carbon dioxide as it descends the column 8. The vapour becomes progressively richer in methane as it ascends the column 8. A liquid fraction comprising 12% by volume of carbon dioxide and 88% by volume of methane collects at the bottom of the column 8 and is withdrawn therefrom by a pump 14. A methane-rich vapour collects at the top of the column 8 and some of this vapour is condensed in the condenser 10 and thus flows back down the column as liquid reflux. Uncondensed vapour which may, if desired, comprise methane and be substantially free of carbon dioxide, or which may include small amounts of carbon dioxide in addition to methane, is taken from the top of the column 8 through the outlet 16 as a product stream. This product stream may be warmed to ambient temperature, thus providing cooling for the incoming stream of methane and carbon dioxide. Alternatively, if the cold product stream additionally contains nitrogen, it may be further processed to reject the nitrogen prior to being warmed to ambient temperature.

The liquid taken from the bottom of the column 8 by operation of the pump 14 is then introduced into a second rectification column 20 operating at a higher pressure than the first rectification column 8. In this example, the rectification column 20 operates at an average pressure of 49.3 atmospheres. In order to raise the temperature of the liquid taken from the bottom of the column 8 to a value at which it can be rectified in the column 20, a heat exchanger 22 is typically employed. Partial or complete evaporation of the liquid may take place in the heat exchanger 22. The heat exchanger 22 may be integrated into a nitrogen rejection plant (not shown). Alternatively, or in addition, it can provide cooling for the stream passing through the pipeline 2.

The rectification column 20 is provided at its top with a condenser 26 so as to provide reflux, and a reboiler 28 at its bottom so as to provide reboil. Similarly to the rectification column 8, the column 20 is provided with suitable distillation trays or plates (or packing) in order to facilitate intimate contact between a descending liquid and an ascending vapour. There is thus mass exchange between the vapour and the liquid. In consequence, the liquid becomes progressively richer in carbon dioxides as it descends the column, and the vapour becomes progressively richer in methane as it ascends the column.

A liquid comprising a major proportion of carbon dioxide and a minor proportion of methane collects at the bottom of the second rectification column 20. Some of this liquid is reboiled and the remainder is withdrawn through an outlet 30. If desired, the stream taken from the bottom of the column 20 may be an essentially pure carbon dioxide product. This is not however essential to the invention, and, alternatively, the carbon dioxide stream may be treated as a waste stream and discharged to the environment after it has been warmed to ambient temperature (in this example by heat exchange with the incoming feed stream).

Some of the vapour reaching the top of the column 20 is condensed, and the remainder is withdrawn through an outlet 34 as a stream containing a mahor proportion of methane and a minor proportion of carbon dioxide (though typically, but not necessarily, the proportion of carbon dioxide is greater than that in the feed stream). The stream withdrawn through the outlet 34 is then expanded through a throttling valve 36 and the resultant fluid is then passed to the pipeline 4 to be united with the incoming feed stream entering the plant through the pipeline 2. It will be appreciated that such recycling of the vapour from the top of the rectification column 20 increases the concentration of carbon dioxide in the fluid entering the first rectification column 8.

Figure 2:
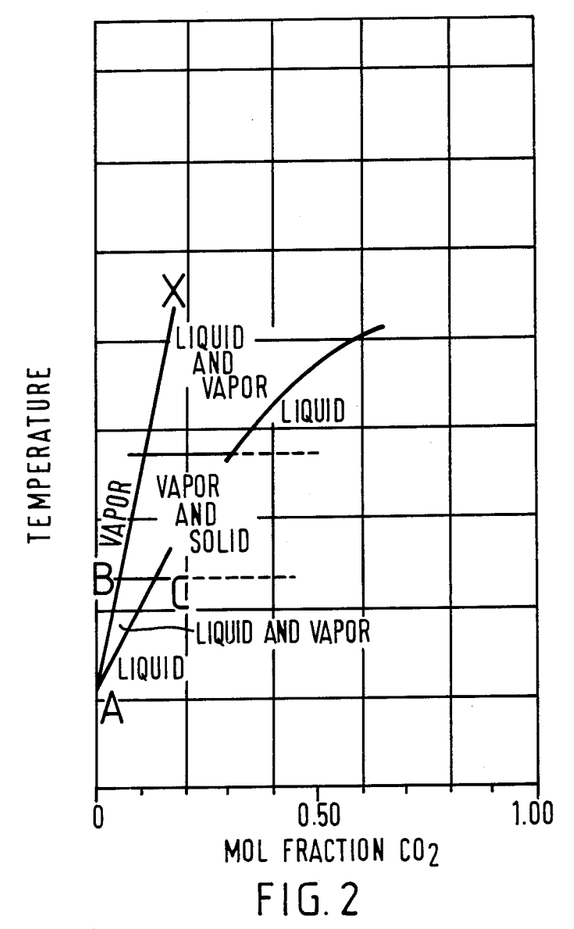
FIG. 2 is a schematic liquid-vapour equilibrium diagram for the carbon dioxide-methane system at a pressure of 41.4 atmospheres absolute.
Figure 3:
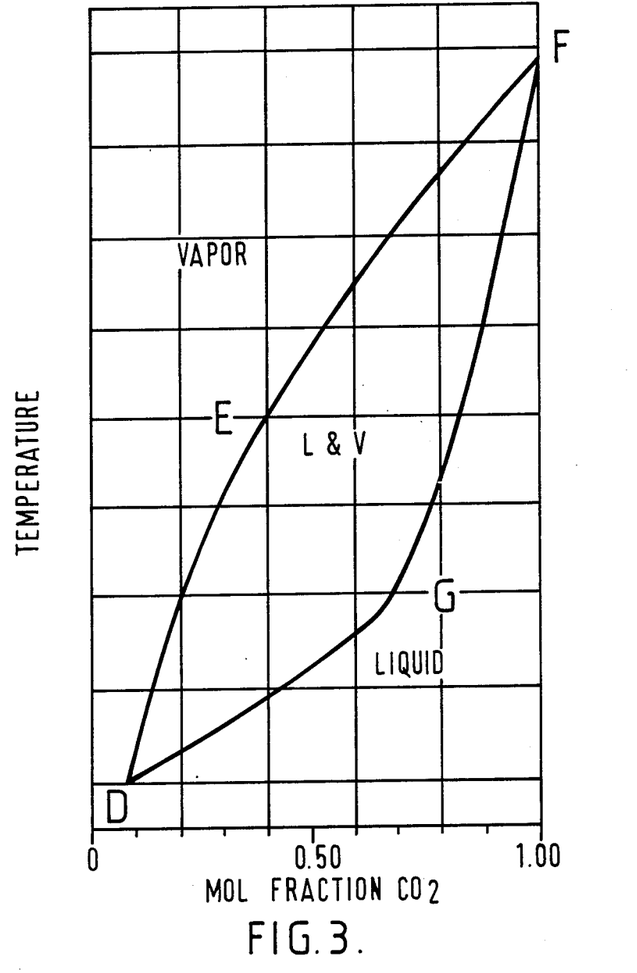
FIG. 3 is a schematic diagram similar to FIG. 2 for the carbon dioxide-methane system at a pressure of 49.3 atmospheres absolute.

FIGS. 2 and 3 both illustrate the constraints that are placed on the selection of the operating pressures for the rectification columns 8 and 20 in FIG. 1 and on the temperatures and compositions of the feeds to these columns. FIG. 2 is a liquid-vapour equilibrium diagram for the carbon dioxide-methane system at the average pressure that obtains in the column 8. It can be seen from FIG. 2 that in order to give relatively pure methane product and to avoid the deposition of solid carbon dioxide, the rectification column has to operate within the confines of the generally triangular area ABC of the phase diagram. At point C the mole fraction of carbon dioxide in the mixture is 0.12. Thus the rectification column 8 needs to be operated such that the concentration of carbon dioxide in the liquid that is produced at the bottom of the column does not exceed 12% by volume. Moreover, the temperature of the gaseous mixture introduced into the inlet 6 will need to be not greater than the temperature of the line BC and this places a further limitation on the maximum amount of carbon dioxide that can be tolerated in the feed to the inlet 6, the point B defining the maximum.

Referring now the FIG. 3, there is shown a similar liquid-vapour equilibrium diagram for the carbon dioxide-methane system at the average pressure that occurs in the second rectification column 20. At such pressure, no limitation is placed on the operation of the column as a result of a need to avoid the formation of solid carbon dioxide.

However, all points within the operating area DEFG are of a higher temperature than any point in the operating area ABC. It is thus preferable when operating the columns 8 and 20 at average pressures of 41.4 and 49.3 atmospheres respectively to raise the temperature of the liquid fraction taken from the bottom of the column 8 to a temperature avove that of the point D. This may also involve at least partially vaporising the liquid. It is necessary that the temperature and composition of the vapour leaving the top of the column 20 are such that after passage through the valve 36, which is effective to reduce the pressure of the vapour to that which obtains in the first column 8 the vapour has a temperature and composition that lie on a point to the left of line BX in FIG. 2.

It can be seen from FIG. 3 that it is not possible to obtain a pure methane fraction at the top of the column 20. In this example, at point D the limiting mole-fraction of carbon dioxide is about 0.09. Thus, the fraction at the top of the column 20 contains a minimum of 9% by volume of carbon dioxide. By recycling this fraction to the lower pressure rectification column 8, it is possible to maintain the composition of the feed gas mixture at a level such that deposition of solid is avoided. The feed gas mixture may contain carbon dioxide than the recycled vapour. The method according to the invention is particularly advantageous if the composition of the feed is such that recycle rate through the pipeline 4 is not excessively high in comparison to the feed rate through the pipeline 2.

In general, the proportion of carbon dioxide in the feed gas mixture will determine the optimum average operating pressures for the columns. The higher the percentage carbon dioxide in the feed gas mixture, the lower is the optimum pressure difference between the two columns.

It will be appreciated that the inclusion of other gases in the feed gas mixture will affect the phase equlibria shown in FIGS. 2 and 3. In general, any nitrogen present will not have a great effect. The presence of higher hydrocarbons will tend to increase the concentration of carbon dioxide that can be handled in the feed gas mixture.

In at least some examples of the separation of a mixture comprising carbon dioxide and methane in accordance with the invention employing the plant shown in FIG. 1, throttling of the stream leaving the top of the column 20 through the valve 36 would cause the stream to enter the vapour-solid region in FIG. 2. Modifications to the plant intended to overcome this problem are illustrated in FIGS. 4 and 5 of the accompanying drawings, in which parts similar to those shown in FIG. 1 are indicated by the same reference numerals as in FIG. 1.

Figure 4:
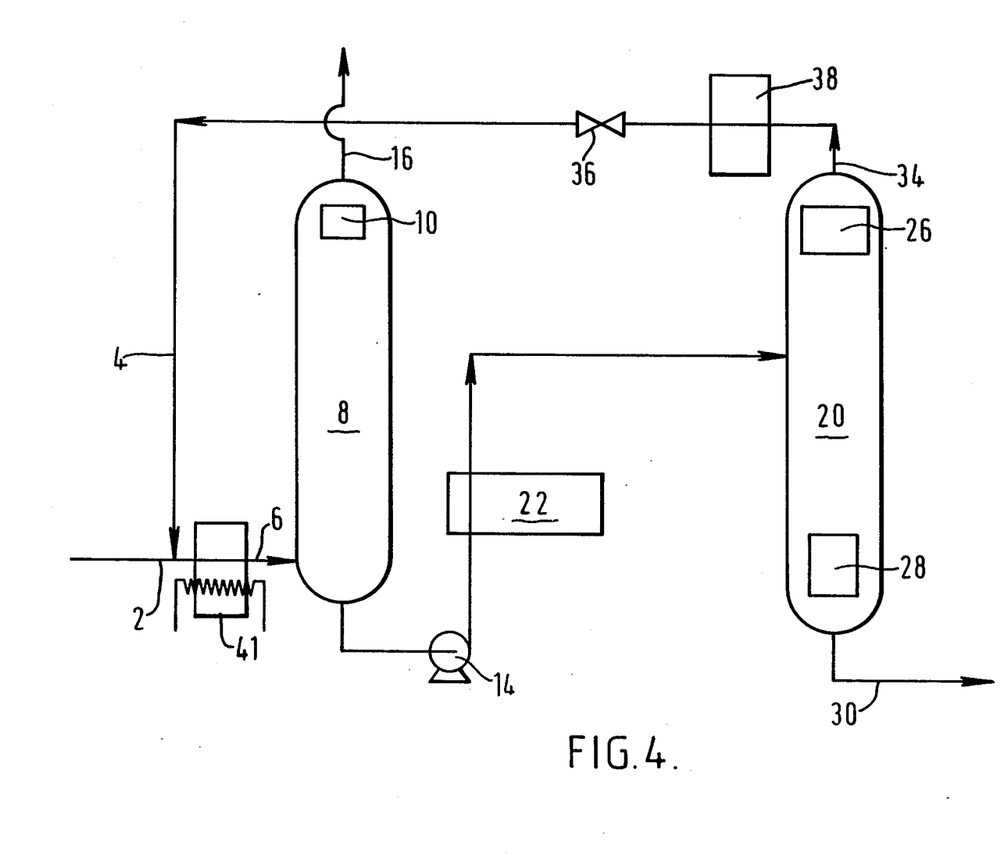
FIG. 4 is a schematic flow diagram illustrating a second plant for performing the invention.

The plant shown in FIG. 4 of the accompanying drawings, in comparison to the plant shown in FIG. 1, has an additional heat exchanger 38. The heat exchanger 38 has means (not shown) for raising the temperature of the vapour leaving the top of the column 20. The heat exchanger 38 is thus operated so as to raise the temperature of this vapour to a value such that after throttling in the valve 36 (with its concomitant temperature reduction) the temperature and composition of the vapour are represented by a point lying to the left of the line BX in FIG. 2 and thus the vapour remains entirely in the vapour phase. Downstream of the throttling valve 36, this vapour is mixed with the feed stream entering the Pipeline 2 to form a mixture whose temperature and composition is such that the mixture lies on or a little to the left of the line AB shown in FIG. 2. If desired, the temperature of the mixture may be admitted by heat exchange in the heat exchanger 41. In other respects the plant shown in FIG. 4 is identical to that shown in FIG. 1.

Figure 5:
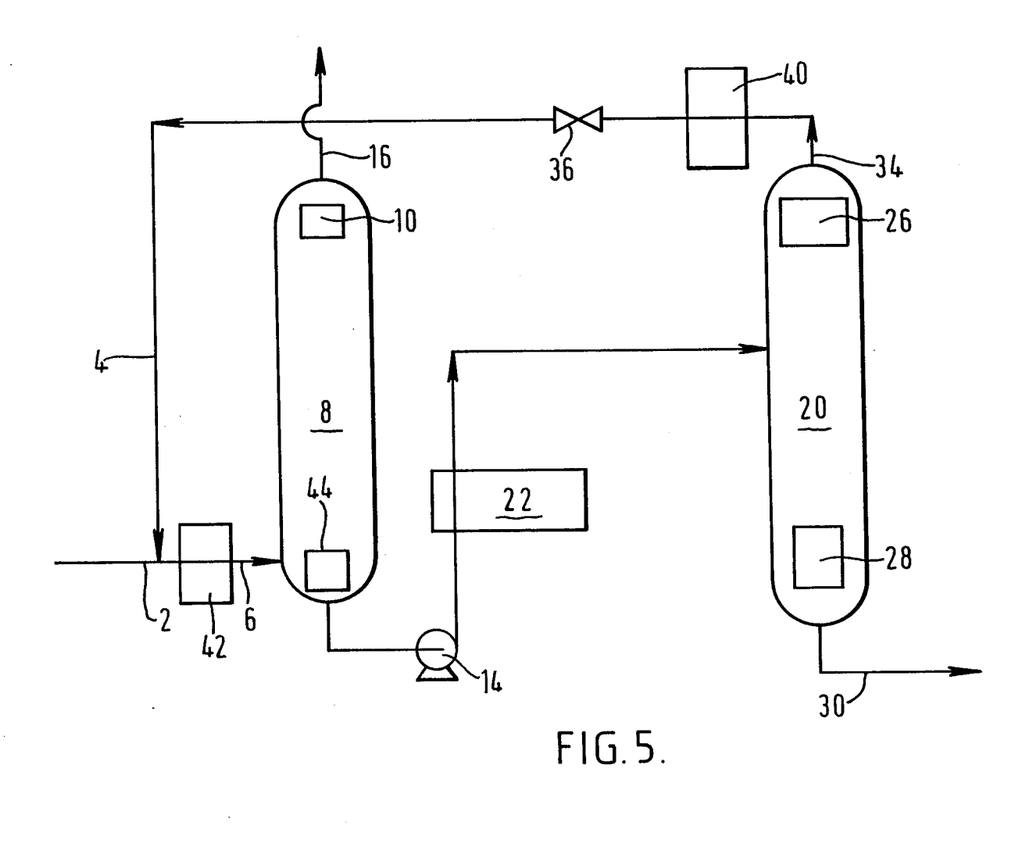
FIG. 5 is a schematic flow diagram illustrating a third plant for performing the invention.

The plant shown in FIG. 5 of the accompanying drawings has an additional heat exchanger 40. The heat exchanger 40 has means (not shown) for lowering the temperature of the vapour leaving the top of the column 30 such that it is first condensed and then sub-cooled to a temperature below that of the in FIG. 2 and such that allowing the throttling valve 36 the fluid has a temperature below that of point C. Thus, on subsequent passage of the liquid through the throttling valve 36 there is no possibility of solid being deposited. After passage through the throttling valve, depending on the respective pressures in the columns 8 and 20 and the temperature at the inlet to the valve 36, the carbon dioxide-methane mixture may remain in the liquid state or be at least partially vaporised. Downstream of the valve 36, the expanded fluid is then mixed with the feed stream passing through the pipeline 2. If desired, the temperature of the mixture may be adjusted by passing it through a heat exchanger 42 upstream of its introduction into the column 8 through the inlet 6. If necessary, the column 8 is provided with a reboiler 44 to provide reboil, and typically there are one or two liquid-vapour contact trays in the section of the column intermediate the feed level and the reboiler. (If desired, the plants shown in FIGS. 1 and 4 may be provided with similar heat exchangers 42 and reboilers 44.) In other respects the plant shown in FIG. 5 is similar to that shown in FIG. 1.

In an alternative embodiment of the plant shown in FIG. 5, rather than being mixed with the fluid passing through the pipeline 2, the fluid from the pipeline 4 is introduced separately into the column 8.

In one example of the method according to the invention, the plant shown in FIG. 4 or FIG. 5 may be used to separate a mixture comprising 93% by volume of methane and 7% by volume of carbon dioxide. The column 8 separates the incoming mixture into a liquid (at the bottom of the column) comprising 12% by volume of carbon dioxide and 88% by volume of methane, and a vapour (at the top of the column) comprising 98.6% by volume of methane and 1.4% by volume of carbon dioxide. The column 20 separates the liquid fraction from the column 8 into a liquid (at the bottom of the column) comprising 90% by volume of carbon dioxide and 10% by volume of methane and a vapour (at the top of the column) comprising 91% by volume of methane and 9% by volume of carbon dioxide. For each 1,000 cubic meters of methane-carbon dioxide (7%) mixture entering the pipeline 2 upstream of its union with the pipeline 4 per unit time, 1681cubic meters of liquid are withdrawn from the bottom of the column 8 per unit time, 937.8 cubic meters of vapour are withdrawn from the top of the column 8 per unit time, and 62.2 cubic meters per unit time of liquid are withdrawn from the bottom of column 28 through the outlet 30.

We claim:

1. A method for separating a mixture comprising carbon dioxide and methane, comprising the steps of feeding said mixture into a first liquid-vapour contact column, performing a first rectification of the mixture therein to form a product vapour fraction containing a reduced concentration of carbon dioxide at the top of the column and a fraction enriched in carbon dioxide relative to said mixture at the bottom of the column, said enriched fraction containing up to about 12 percent by volume of carbon dioxide, subjecting the carbon dioxide-enriched fraction to a second rectification in a second liquid-vapour contact column operating at a higher pressure than said first column and thereby forming at the bottom of the second column a liquid fraction in which carbon dioxide predominates, and at the top of the second column a vapour fraction containing a lower proportion of carbon dioxide than the carbon dioxide enriched fraction, and returning fluid from at or near the top of the second column to the first column, the concentrations of carbon dioxide in the said gaseous mixture and in the said carbon dioxide-enriched fraction, and the operating pressures in the columns being selected so as to avoid the deposition of solid carbon dioxide.

2. A method according to claim 1, in which the first column operates at a pressure of about 41 atmospheres.

3. A method according to claim 1, in which the higher pressure column operates at a pressure of about 49 atmospheres absolute.

4. A method according to claim 1, in which the mixture of methane and carbon dioxide includes up to 10% by volume of carbon dioxide.

5. A method according to claim 1, additionally including the steps of taking a stream of the enriched fraction from the bottom of the first column and heating the stream to raise its temperature prior to its being rectified in the second column.

6. A method according to claim 1, in which said fluid withdrawn from at or near the top of the second column is adjusted in temperature to avoid deposition of solid carbon dioxide at the operating pressure of the first column and is then throttled upstream of where it is returned to the first column.

7. A method according to claim 6, in which said fluid is taken as vapour and said adjustment comprises the step of raising the temperature of the fluid such that on throttling it remains in the vapour phase.

8. A method according to claim 6, in which said fluid is taken as vapour and the temperature adjustment comprises condensing the vapour and sub-cooling the condensate such that on throttling its temperature is sufficiently low for there to be no deposition of solid carbon dioxide.

9. A method according to claim 6, in which after being throttled, said fluid is united with the feed stream of carbon dioxide and methane upstream of the first column.

10. A method according to claim 6, in which said fluid after being throttled is introduced into the first column separately from the feed gas mixture.

11. A method according to claim 1, in which the gaseous mixture additionally includes nitrogen and/or one or more hydrocarbons other than methane.

* * * * *